(12) United States Patent
Kurland et al.

(10) Patent No.: US 9,771,400 B2
(45) Date of Patent: Sep. 26, 2017

(54) PHOTOACTIVE SILK PROTEIN AND FABRICATION OF SILK PROTEIN STRUCTURES USING PHOTOLITHOGRAPHY

(71) Applicant: VIRGINIA COMMONWEALTH UNIVERSITY, Richmond, VA (US)

(72) Inventors: Nicholas E. Kurland, Virginia Beach, VA (US); Vamsi K. Yadavalli, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 146 days.

(21) Appl. No.: 14/765,016

(22) PCT Filed: Jan. 31, 2014

(86) PCT No.: PCT/US2014/013986
§ 371 (c)(1),
(2) Date: Jul. 31, 2015

(87) PCT Pub. No.: WO2014/123761
PCT Pub. Date: Aug. 14, 2014

(65) Prior Publication Data
US 2015/0376248 A1 Dec. 31, 2015

Related U.S. Application Data

(60) Provisional application No. 61/761,266, filed on Feb. 6, 2013.

(51) Int. Cl.
| | |
|---|---|
| *G03F 7/038* | (2006.01) |
| *C07K 14/435* | (2006.01) |
| *C07K 1/107* | (2006.01) |
| *G03F 7/20* | (2006.01) |
| *G03F 7/26* | (2006.01) |

(52) U.S. Cl.
CPC ...... *C07K 14/43586* (2013.01); *C07K 1/1072* (2013.01); *C07K 1/1077* (2013.01); *G03F 7/038* (2013.01); *G03F 7/0388* (2013.01); *G03F 7/20* (2013.01); *G03F 7/26* (2013.01)

(58) Field of Classification Search
CPC . G03F 7/038; G03F 7/0388; C07K 14/43586; C07K 1/1077; C07K 1/1072
USPC ............... 430/287.1, 325, 9, 18; 530/353
See application file for complete search history.

(56) References Cited

U.S. PATENT DOCUMENTS

| | | | |
|---|---|---|---|
| 6,589,736 B1 * | 7/2003 | Rothschild | A61K 41/0042 435/5 |
| 2002/0111673 A1 | 8/2002 | Holton et al. | |
| 2004/0170827 A1 | 9/2004 | Crighton et al. | |
| 2009/0232963 A1 | 9/2009 | Kaplan et al. | |
| 2010/0075297 A1 * | 3/2010 | Lawrence | C07K 1/02 435/4 |

FOREIGN PATENT DOCUMENTS

WO  2010/057142 A2  5/2010

OTHER PUBLICATIONS

Furuzono et al., "Chemical modification of silk fibroin with 2-methyacryloyloxyethyl phosphorylcholine. II. Graft-polymerization onto fabric through 2-methacryloyloxyethyl isocyanate and interaction between fabric and platelets", Biomaterials, Feb. 200, pp. 327-333, vol. 21, No. 4.
Teramoto et al., "Chemical Modification of Silk Sericin in Lithium Chloride/Dimethyl Sulfoxide Solvent with 4-Cyanophenyl Isocyanate", Biomacromolecules, 2004, pp. 1392-1398, vol. 5.

* cited by examiner

*Primary Examiner* — John A McPherson
(74) *Attorney, Agent, or Firm* — Whitham, Curtis & Cook

(57) ABSTRACT

A natural protein, specifically silk fibroin or sericin, is chemically modified such that it can be rendered photoactive, but which otherwise has similar structure and attributes as silk fibroin or sericin. This chemically modified silk conjugate can be patterned using radiant energy to produce patterned silk materials which may be used for a wide variety of applications such as making micro and nanoparticles of different shapes and functionalities for drug delivery, creating new forms of intricate 3D scaffolds for tissue engineering, and forming substrates for flexible bio-electronics.

23 Claims, 10 Drawing Sheets

PHOTOACTIVE SILK PROTEIN AND FABRICATION OF SILK PROTEIN STRUCTURES USING PHOTOLITHOGRAPHY

FIELD OF THE INVENTION

The present invention generally relates to chemical modification of a natural protein to render it photoactive and, more specifically, the rendering of silk protein photoactive and creation of silk protein (micro)structures by photopolymerization.

BACKGROUND

The design and fabrication of precise spatial patterns, microstructures, and nanostructures of peptides and proteins have widespread applications in tissue engineering, cellular biology, molecular electronics, biosensors, photonics, delivery of biomolecules, and therapeutics. Micro and nanostructured scaffolds and cellular substrates in two and three dimensions can directly influence the spatial organization of tissues and organs. Engineered structures of peptides, proteins, and DNA have applications in the delivery of bioactive molecules and therapeutics. The spatial arrangement of biomolecules in a controlled manner on a surface can enable fundamental biochemical analyses of complex systems, screening, and multiplexed assays. Periodic structures have the ability to manipulate the passage of light resulting in novel metamaterials and photonic crystals. To achieve these structures, diverse techniques including self-assembly, soft lithography, and photolithography have been reported.

Known approaches to spatially arrange proteins have relied on passive, substrate-based methods in which chemical modifications to the substrate induce preferential regions for adhesion. In three dimensions, the ability to spatially pattern proteins can enable the formation of intricate scaffolds for the growth of cells in scaffolds. To date, this has been restricted to simplistic architectures achieved using methods such as casting alone. Such methods do not provide adequate micro and nanoscale control.

Photolithography ("writing using light") using ultraviolet to visible light has been widely used in the semiconductor industry to pattern materials and fabricate circuits of extraordinary complexity with microstructured spatial morphologies. However, a primary requirement for such light activated processes is that the material they act upon must be light sensitive, i.e. photocurable. This has limited the scope of application of photolithography to a narrow base of starting materials, typically synthetic polymers. One approach to directly pattern proteins has been to alter them chemically or biochemically to render them intrinsically photoreactive. Examples include photactivable derivatives of biotin, and elastin-like proteins with photo-reactive, non-canonical amino acids incorporated via site-specific and residue-specific techniques. To date, neither of the strategies described have been shown with intact naturally available biopolymers. Significantly, light-based systems that can handle different compositions of proteins are not efficiently developed. Thus, the development of a modified photolithography platform is attractive as a means of directly producing spatially-immobilized biomolecules in 2D and 3D.

Silks have a rich history as a biomaterial either by themselves or blended/complexed with polymers, ceramics and gold. Silkworm silk, in particular, is a unique biocompatible material that has used in textile processing and medical applications for thousands of years. Silk exists in a self-assembled fibrous configuration, in which mechanically robust fibroin (70%) comprises the core of the silk fiber, and a glue protein sericin (30%) surrounds this core. Silk is classified as an FDA approved material and defined by the USP as a nondegradable material because it retains over 50% of its tensile strength 60 days post-implantation in viva.

Silk fibroin, in contrast to naturally occurring silk comprising both the proteins fibroin and sericin, is the more commonly used biomaterial. It is slowly absorbed in vivo and degrades over time based on several different factors, with typical proteolytic degradation and resorption within a year. In contrast to synthetic materials, the degradable behavior of silk fibroins does not result in an adverse immunogenic response. This is significant advantage over materials that have the potential to create adverse reactions either by themselves or due to their degradation products in vivo. Developing new processing strategies to enhance fibroin applications therefore has great biomedical potential.

Furuzono et al. (Chemical modification of silk fibroin with 2-methacryloyloxyethyl phosphorylcholine. II. Graft-polymerization onto fabric through 2-methacryloyloxyethyl isocyanate and interaction between fabric and platelets. Biomaterials, 2000. 21(4): p. 327-333) describes work on isocyanate addition to a silk protein, using 2-Methacryloyloxyethyl isocyanate/isocyanatoethyl methacrylate (MOI/ICEMA). This group acted as a stepping stone for adding a further functionality onto silk 'fabric' or degummed fiber. Furuzono did not solubilize the silk protein and substantially lost the isocyanate functionality upon further reaction.

Teramoto et al. (Chemical Modification of Silk Sericin in Lithium Chloride/Dimethyl Sulfoxide Solvent with 4-Cyanophenyl Isocyanate. Biomacromolecules 2004, 5, (4), 1392-1398) took advantage of similar chemistry a few years after Furuzono's work. Teramoto et al. used a solvent system of 1M LiCl/DMSO, to achieve isocyanate addition on solubilized sericin but did not contemplate or address making sericin photoreactive.

SUMMARY

To date, micro-architectures of silk have been formed using techniques such as imprinting, molding via soft-lithography, electrospinning, embossing, and inkjet printing. In the case of molding via soft lithography, silk is brought into contact with molds and cured to impart desired patterns. Embodiments of the invention provide methods for forming micro and nanoarchitectures of silk using optical methods.

Optical lithography using proteins may be achieved in two ways: a) using well-developed, traditional chemical photolithographic processes to create surface adhesive sites for site-specific protein attachment, or b) altering the biochemical properties of proteins chemically by attachment of photoreactive functional groups such as arylazides and nitrobenzyls. This allows the protein to be crosslinked in the presence of light in a specific pattern as defined by a photomask and the uncrosslinked protein can be washed away to reveal the designed shapes. One approach to achieve the latter is the development of intrinsically photoreactive proteins that can function as a "photoresist" without the need for post-translational chemical modification. This has been achieved via the incorporation of photo-reactive, non-canonical amino acids into proteins via site-specific and residue-specific techniques. However, this protein engineering approach can generally be complex and expensive and can potentially compromise protein function.

Provided is a novel approach to chemically modify natural proteins to prepare stable, photolabile biopolymers. Specifically, this work focuses on the silk proteins fibroin and sericin to form light activated protein conjugates that can form features at sub-micrometer resolution for a wide range of applications. The photoactive silk protein conjugates may be used to produce rapidly patterned protein architectures. In exemplary embodiments, the protein architectures may have dimensions and resolutions variable up to 4 orders of magnitude (1 μm to cm).

An advantage of the present invention is effectively solubilizing silk fibroin and sericin such that there is protection/preservation of the photoreactive functionality of a fibroin or sericin conjugate. Dissolving and modifying fibroin and sericin to a non-fibrous state helps with using silk as a building block as opposed to conducting modifications to simply change the surface chemistry of silk protein fibers.

While optical lithography has been used to indirectly pattern proteins in prior works, direct patterning of proteins to form high fidelity and high-resolution structures remains an existing challenge addressed by the present application. The use of silk as a scaffold biomaterial hews to the traditional paradigm of tissue engineering simplistic architectures such as sheets, fibers, or porous scaffolds. The biocompatibility of both fibroin and sericin make them ideal for applications involving cells, enhancing cell attachment, improving cellular growth, and accelerating proliferation when added to culture media. The augmentation of naturally-occurring silk proteins with photoreactive properties is a novel concept.

Silk proteins are a class of chemically diverse polypeptides with complex structure and functionalities. Embodiments of the invention enable retention of the function and attributes of sericin and fibroin silk proteins as patterned structures. To develop a platform for generating functional patterns of silk proteins, a means of facile chemical conjugation is provided herein which yields photoactive silk protein conjugates that have the same function and attributes of sericin and fibroin silk proteins. Fibroin provides over 20% modifiable amino acids to allow chemical conjugation without significant modification of protein structure and function. Site-specific modification allows preservation of the core sequences of sericin and fibroin (e.g., in some embodiments, the primary structure of sericin and fibroin is maintained; there may also be retention of β-sheet formation of fibroin via modifications outside of -Gly-Ala-Gly-Ala-Gly-Ser-core sequence). Silk protein is readily available and the relatively simple synthesis protocol permits manufacturing scalability.

A photolithography process allows formation of complex architectures that can be tailored not only in terms of shapes and sizes but also in terms of mechanical properties by simply altering the crosslinking density. This can be accomplished by the control of silk protein and photoactive constituents during the process of making silk protein conjugates or by control of the photoinitiator and by other means. Photolithography provides an option to rapidly and directly fabricate complex features with high fidelity and without the need for high temperature and pressure or molding masters. New silk conjugate materials may be used with 2D and 3D printing methods to form scaffolds with nano and microstructural anisotropy and in-built biochemical cues for enhanced tissue function. There are wide ranging applications, including applications in biological arrays, tissue engineering, and drug delivery.

DETAILED DESCRIPTION

Figure 1A:
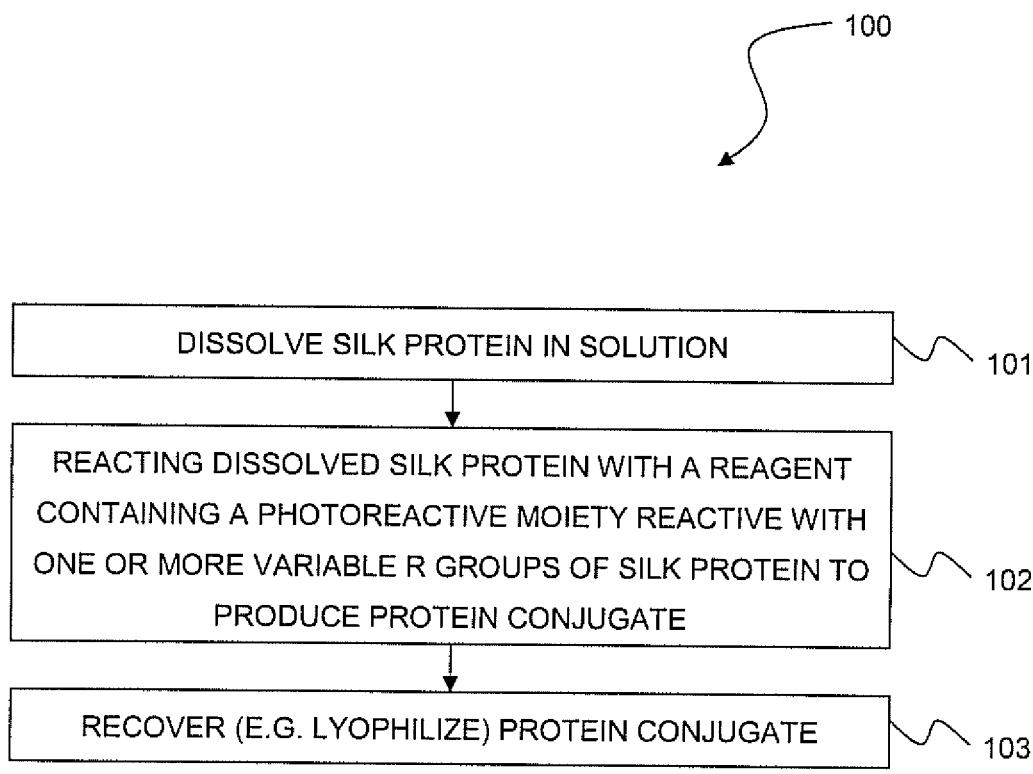
FIGS. 1A and 1B are flowcharts of methods for making photoactive silk proteins.

Referring now to the drawings, more particularly FIG. 1A, a general method 100 of making photoactive silk protein is shown. Method 100 is particularly well suited for fibroin as well as sericin. Generally, where exemplary embodiments described herein are discussed in reference to fibroin, sericin may likewise be used unless the context indicates otherwise. Method 100 as well as other processes and steps may also be applied to sericin and/or other natural (i.e. non synthetic) proteins.

At step 101, silk protein (e.g. fibroin or sericin) protein is dissolved. This may be regarded as activating the fibroin or sericin. Suitable extraction and purification techniques of silk fibroin or sericin from, for example, *Bombyx mori* silkworm cocoons are well known in the art. Purified protein may also be obtained from commercial vendors, e.g. purified sericin may be purchased from Wako Chemicals USA, Richmond, Va. After the silk protein molecules are dissolved/activated, they are combined at step 102 with a reagent containing at least one photoreactive moiety reactive with one or more variable R groups of fibroin or sericin. The resulting product of the reaction between the activated silk protein and reagent is a (photoactive) fibroin/sericin conjugate. Note that the terms photoactive and photoreactive may generally be used interchangeably. Different reagents having photoreactive moieties may be used in accordance with method 100 provided that core sequences of the natural/native silk protein are retained in the conjugate product. In the case of fibroin, the reaction of the fibroin and the reagent should result in a fibroin conjugate which retains β-sheets of -Gly-Ala-Gly-Ala-Gly-Ser-core sequence of natural fibroin protein. Photo-(re)active additions to fibroin may be achieved by taking advantage of one or more variable R groups in the protein structure, namely primary amines ($NH_2$, e.g. lysine), carboxyls (—COOH, e.g. aspartic acid and glutamic acid), sulfhydryl groups (—SH, e.g. cysteine), and hydroxyls (—OH, e.g. serine, threonine, and tyrosine). Any associated or modified proteins containing such reactive groups may also be used in alternative embodiments.

A reagent in step 102 may be a reagent proposed herein or other commercially-available reagents (e.g. methacrylic acid N-hydroxysuccinimide ester). Appropriate photoreactive moieties/groups for step 102 may include but are not limited to acrylates, methacrylates, and vinyl ethers as depicted for exemplary purposes below.

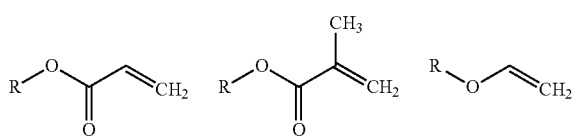

Photopolymerizable end groups (A) acrylate
(B) methacrylate (C) vinyl ether

These photoactive moieties/groups are the most common and versatile. Crosslinking may also be achieved from multifunctional monomers, mainly acrylates (telechelic oligomers, monoacrylates or diacrylates) or unsaturated polyesters, multifunctional epoxides, vinyl ethers, or thiol-polyenes. Hybrid systems are also possible, with examples including vinyl ether/acrylate combination, vinyl ether/epoxide, vinyl ether/unsaturated ester, and epoxide/acrylate. Other photopolymerizable groups which may be used are discussed in U.S. Pat. No. 4,537,855 to Hiroshilde which is herein incorporated by reference. Disclosed therein are photopolymerizable photosensitive resins having polyfunctional ethylenically unsaturated groups in the side chains or end groups thereof. Polyfunctional ethylenically unsaturated groups which may be used in accordance with the present application have, for example, a structural unit of the following general formula:

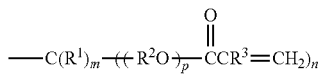

(in which $R^1$ represents a hydrogen atom, an alkyl group such as methyl, ethyl or the like, and a hydroxyalkyl group such as hydroxymethyl, hydroxyethyl or the like, $R^2$ represents an alkylene group such as methylene, ethylene, trimethylene or the like, $R^3$ represents hydrogen atom or methyl, m is 0 or 1 and n is 2 or 3 provided that m+n=3, and p is an integer of 1 to 3). Specific examples of the polyfunctional ethylenically unsaturated compounds include pentaerythritol triacrylate, pentaerythritol trimethacrylate, pentaerythritol diacrylate, pentaerythritol dimethacrylate, trimethylolethane diacrylate, trimethylolethane dimethacrylate, trimethylolpropane diacrylate, trimethylolpropane dimethacrylate, dimethylolmethanol diacrylate (glycerol-1,3-diacrylate), dimethylolmethanol dimethacrylate (glycerol-1,3-dimethacrylate), trimethylolmethane diacrylate, trimethylolmethane dimethacrylate, trimethylolpropane triacrylate, trimethylolethane triacrylate, and pentaerythritol tetraacrylate, and the like.

At step 103, the silk protein conjugate is recovered from the reaction solution. Recovery generally provides isolation/separation of the conjugate from, for example, reaction byproducts and unreacted native silk protein and reagent. A recovered purified product may take a variety of forms, including a powder, gel, suspension, or some other composition. Conjugate recovery at step 103 may be achieved by drying the conjugate, such as by lyophilization, to yield a stable and storable solid. An exemplary product of method 100 is a powdered fibroin or sericin conjugate. Two example products are fibroin methacrylate (FMA) and sericin methacrylate (SMA).

Figure 1B:
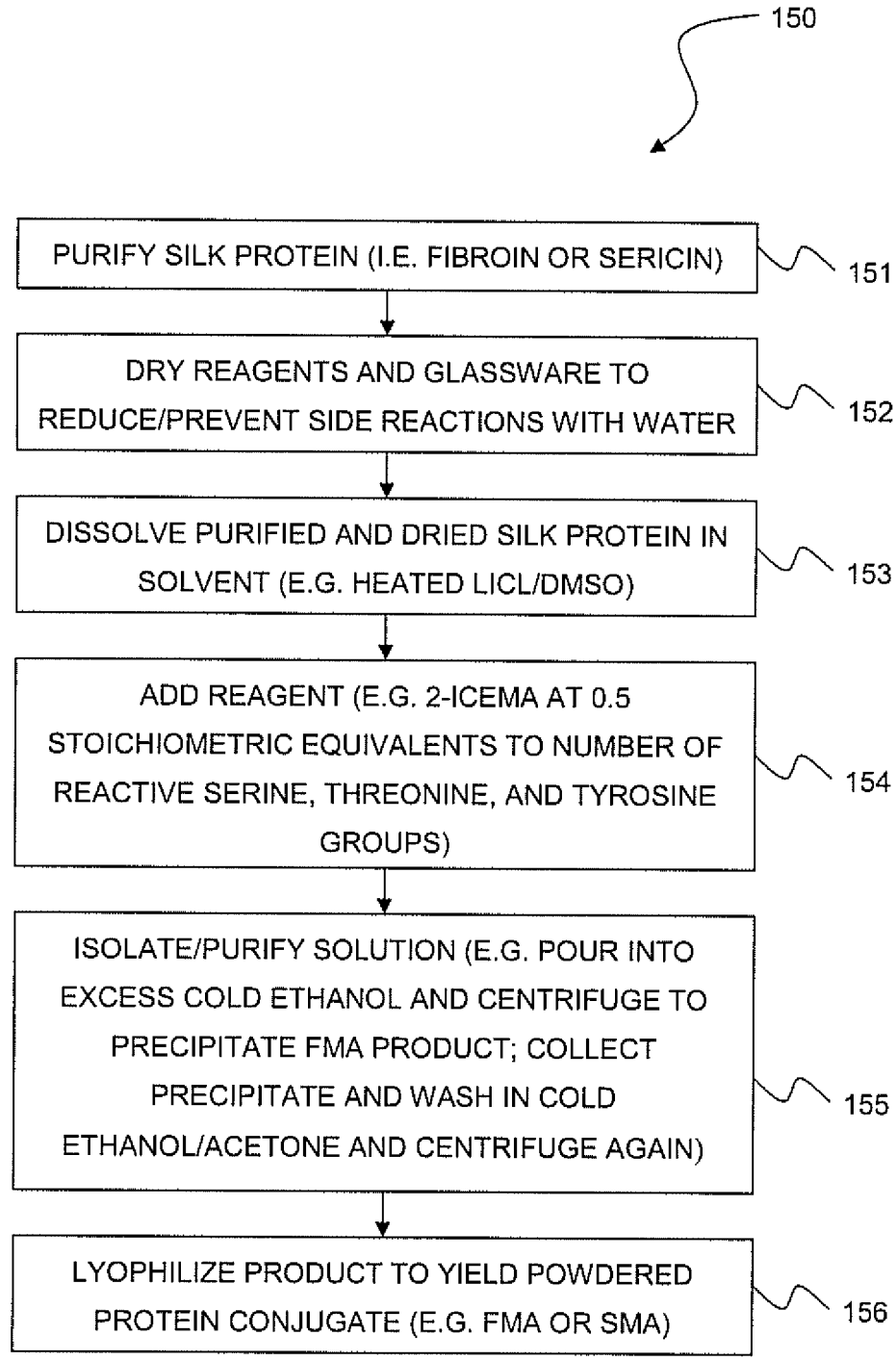

Referring now to FIG. 1B, method 150 is consistent with method 100 but presents a number of exemplary material and processing step selections. When starting with the basic and original natural material—silk cocoon—silk fibroin protein (e.g. fibroin or sericin) may first be purified by known techniques as indicated at step 151. Prior to reacting the purified fibroin or sericin with a reagent, it is generally advantageous to perform any necessary preparatory steps which minimize side reactions, thus improving the yield and purity of the final product of the intended main reaction. An exemplary reagent having a (photoreactive) methacrylate moiety is 2-isocyanatoethyl methacrylate (2-ICEMA), which is reactive with water. Thoroughly drying all reagents and reaction vessels at step 152 reduces/prevents side reactions like hydrolysis and decomposition of 2-ICEMA. According to an example implementation of method 150, fibroin was initially added to a round-bottom flask and vacuum-dried for 24 hours at 70° C. to remove residual water, and LiCl was dried at 120° C. for 24 hours before use.

At step 153, the purified (and dried) fibroin or sericin should be combined with a solvent or solution serving to dissolve the purified protein. As one example, a mixture of lithium chloride (LiCl) and dimethyl sulfoxide (DMSO) may be used as a solvent for fibroin in particular. Other suitable solvents may also be used. According to a particular implementation of method 150, purified fibroin was dissolved at a concentration of 1% (w/v) in 1M LiCl/DMSO, while heating the solution at 60° C. for 45 minutes. As will be apparent to those in the art, heating can accelerate the rate of dissolution but is not necessarily required depending on the choice of solvent. Drying as discussed in relation to step 152 may be repeated at various stages of method 150 to ensure little to no water is present in the solution and therefore reacting with reagents such as 2-ICEMA. In some exemplary embodiments, the mixture was continuously stirred under a dry $N_2$ purge throughout the dissolution in step 153. The solution was cooled and vacuum dried overnight to remove residual water.

Dissolution and activation of fibroin may also be achieved by, for example, a LiBr solution. In the case of sericin, dissolution may be achieved entirely with water or with a chemical solution such as LiCl/DMSO. Once dissolved, the fibroin or sericin protein solution may be dialyzed and lyophilized to yield a fibrous product which is readily water-soluble, in addition to being soluble in 1,1,1,3,3,3-hexafluoro-2-isopropanol (HFIP).

Figure 2A:
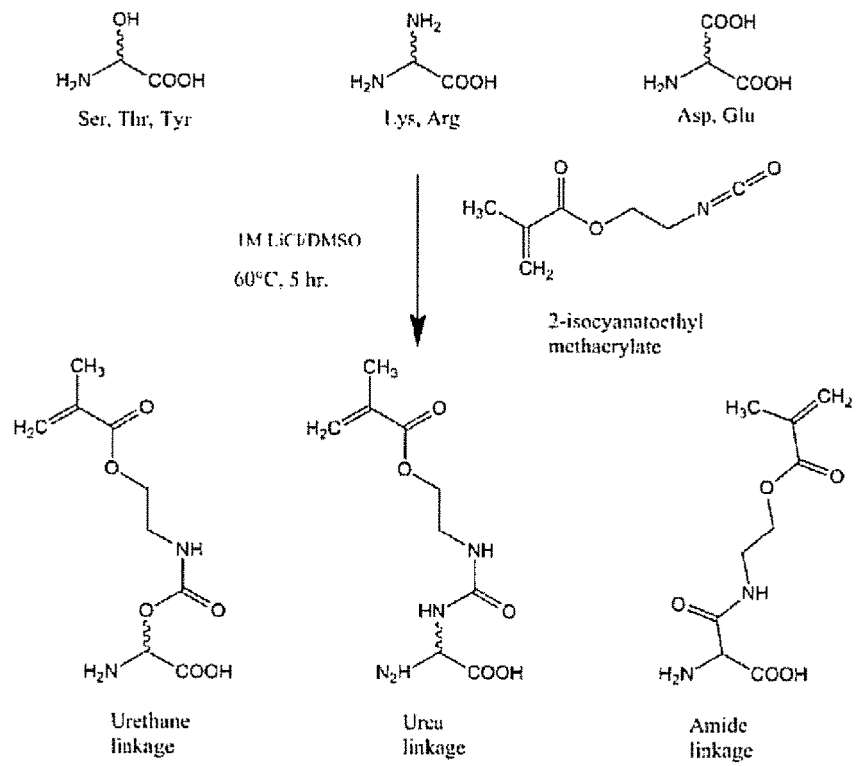
FIGS. 2A and 2B show reaction pathways relevant to making photoactive silk protein.

At step 154, a reagent having one or more photoreactive moieties should be added subsequent to dissolution and activation of the purified protein. In particular exemplary embodiments, 2-ICEMA was added at 0.5-1.0 stoichiometric equivalents to the number of reactive serine, threonine, and tyrosine groups of fibroin. The reaction was stirred and maintained at 60° C. for 5 hours in a dry nitrogen atmosphere. Depending on how one wishes to tailor the final crosslinked product, the stoichiometric ratio may be varied considerably. For example, when the stoichiometric equivalents of photoreactive moiety to reactive serine, threonin, and tyrosine groups of fibroin or sericin (as well as other reactive groups as illustrated in FIG. 2A) ranges from 0.05 to 0.2 the final product after photoactivation will be more gelatinous and softer in nature while when the stoichiometric equivalents is higher, e.g., excess (>1.0) photoactive moiety to the number of reactive serine, threonine, and tyrosine groups of fibroin or sericin (depending on the silk protein employed) the final product can be very dense and highly crosslinked. Upon satisfactory reaction of the fibroin and photoreactive moieties of the reagent, the resulting solution may be purified at step 155. Dialysis is one of various suitable purification options. Per a specific exemplary embodiment, purification was conducted to separate out insoluble fibroin-methacrylate (FMA) product from water-miscible DMSO and soluble 2-ICEMA oligomers and decomposition products. The protein conjugate solution resulting from step 154 was, at step 155, poured into excess cold ethanol and centrifuged to precipitate the fibroin conjugate, e.g., FMA in an exemplary embodiment. The product was collected and washed in a mixture of cold ethanol/acetone and centrifuged. Lyophilization may be performed at step 156, which in the case of FMA yields a light brown powder. In the case of sericin methacrylate (SMA), lyophilization at step 156 yields a pure white powder. Conversion of all reactive groups and complete removal of decomposed reagent (e.g. 2-ICEMA for fibroin or sericin) from the reaction product is not strictly necessary to achieve the desired photoreactivity of the fibroin conjugate product or sericin conjugate product. In a test case, recovery was achieved at 100.0 mg product of the 111.0 mg fibroin at the start of the reaction, i.e. 90.1% recovery.

The presence of the photoreactive moiety in the protein conjugate may be verified as an additional step. In the case of FMA, the conjugate typically shows peaks from 2-ICEMA at 1725 cm-1 (alkene) and at 1635 cm-1 (ester) when verified by attenuated total reflectance (ATR) of Fourier-transform infrared (FTIR) spectra from a spectrophotometer. Similarly, ultraviolet-visible spectroscopy may be employed to determine differences in A280 values between unmodified fibroin and fibroin conjugates.

As already noted, methods 100 and 150 can be adapted to produce different photoactive silk protein conjugates. Alternative photocrosslinkable moieties such as cinnamate functionalities, potentially added to hydroxyl-containing amino acids through partial esterification with cinnamoyl chloride, are capable of undergoing [2+2] cycloaddition when irradiated, effectively acting as a negative photoresist materials. Polyester poly(propylene fumarate) is capable of photocrosslinking in the presence of an initiator, similar to acrylates. Other chemical species, namely azides (—N=N=N), such as aryl azides, or diazirines, such as photoactive amino acids L-photo-leucine and L-photo-methionine, enable hetereobifunctional photocrosslinking at 330-370 nm, through direct-to-peptide reactions (i.e. crosslinker-crosslinker reactions do not occur) or bisazide coupling.

A preferred embodiment is that the silk protein retains certain initial properties. More specifically, core sequences of natural fibroin or natural sericin should be retained/preserved in a silk protein conjugate according to the present invention. Silkworm silk proteins, fibroin and sericin, possess unique 'core' sequences on which the structure and function of such proteins is dependent. Silk fibroin is comprised of a self-organized structure of hydrophobic β-crystalline domains, which are predominantly composed of glycine-X repeats, where X is alanine, serine, threonine, or valine. Within these domains are subdomain oligopeptide motifs (e.g. GAGAGS, GAGAGY, GAGAGA, and GAGYGA), which are rich in glycine, alanine, and serine. Self-assembly of these β-sheet-rich core sequences produces highly crystalline regions within the protein nanostructure, which imparts the fibroin microarchitecture with high tensile strength, elasticity, and overall toughness. Sericin possesses a similar structure, based on a core sequence of serine-rich repeats. This hydroxyl-dominated sequence allows for polar zipper interactions, which are central to β-sheet-rich regions. In sericin, this sequence of serine repeats is further implicated in bioactive functionality.

If desired, processes of making fibroin or sericin conjugate such as methods 100 and 150 may contain an additional step of assessing protein structure after the conjugation process. Circular dichorism (CD) is one possibility for this assessment step, providing a measure of secondary structural content (e.g. α-helical and (β-sheet) through the differential interactions of such structures with circularly polarized light. Ideally, the introduction of the photoreactive moiety (e.g. a methacrylate moiety) should present little change in secondary structure, preserving the native mechanical properties of the protein. Test results conducted on FMA and unconjugated fibroin indicated similar secondary content (25% beta-sheet, <10% alpha helix) for both proteins, showing that the chemical modifications did not affect the core structural properties of fibroin. Circular dichroism is generally performed using a circular dichroism spectrophotometer and employs reference data such as that which is available via Dichroweb using the SELCON3 secondary structure reference database.

Silk, reagents, and other materials for use with the invention may be obtained from a wide variety of sources such as established commercial chemical manufacturers. Pure sericin protein can be purchased from, for example, Wako Chemicals USA, Richmond, Va. Companies such as Sigma-Aldrich (Saint Louis, Mo.) are possible sources for such chemical as anhydrous dimethyl sulfoxide (DMSO), 1,1,1,3,3,3-Hexafluoro-2-propanol (HFIP), 2-isocyanatoethyl methacrylate (2-ICEMA, or IEM) 98% with <0.1% BHT inhibitor, and 3-(Trichlorosilyl) propyl methacrylate (TPM). Analysis grade lithium chloride (LiCl) may be obtained from Acros Organics (Pittsburgh, Pa.). Photoinitiators such as Darocur 1173 and Irgacure 2959 can be obtained from, e.g., Ciba Specialty Chemicals (Tarrytown, N.Y.).

Figure 2B:
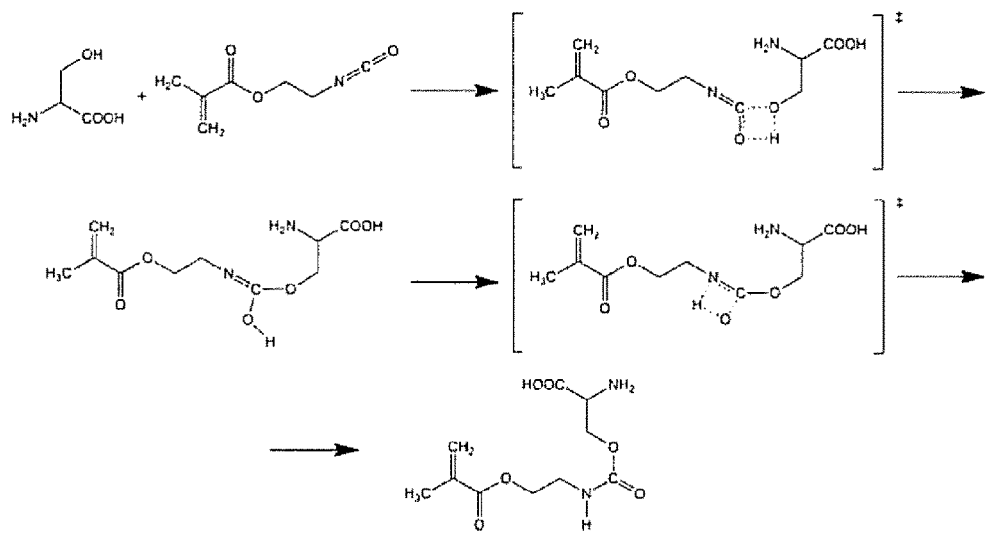

FIGS. 2A and 2B show reaction pathways according to the invention. Reactive groups such as methacrylate and multifunctional acrylate groups in general are well suited targets for conjugation due to their prevalence in existing photolithography techniques, ease of use, and possibility for high-resolution, microscale features. Furthermore, it is generally beneficial to use photoactive groups which readily react with commercially available photoinitiators. The reagent 2-ICEMA is an exemplary reagent for conjugation to fibroin due to the relative ease of reaction with hydroxyl terminated amino acids serine, threonine and tyrosine (12.1 mol % Ser, 0.9 mol % Thr, 5.2 mol % Tyr). To a lesser extent, the isocyanate moiety is reactive with carboxylic acid and amide-terminated amino acids, composing ~2.6% of fibroin's residues. 2-ICEMA is also a suitable reagent for the hydroxyl-rich sericin (~36 mol % Ser, 9 mol % Thr, 3 mol % Tyr). Use of 2-ICEMA as the reagent provides for production of the particular fibroin conjugate called fibroin-methacrylate (FMA) or sericin conjugate called sericin-methacrylate (SMA).

As discussed previously, side reactions should be considered in selection of an appropriate reagent. 2-ICEMA undergoes a process of oligomerization in the presence of DMSO, in addition to degradation in the presence of water resulting in the evolution of $CO_2$. These side reactions may compete with the fibroin conjugation process to decrease the overall yield of fibroin-methacrylate conjugates and should therefore be minimized. FIG. 2B demonstrates for exemplary purposes the reaction between 2-ICEMA and either hydroxyl-terminated amino acids or water molecules. As will be appreciated, a wide variety of photoreactive moieties may be covalently bonded to the backbone of fibroin and sericin silk proteins in a controlled fashion to produce photoactive silk protein conjugates which behave like the unmodified silk proteins in terms of their performance characteristics, but which can be patterned using radiant energy to produce patterned microstructures of crosslinked silk proteins.

Considering the two components of silkworm silk, namely sericin and fibroin, 74.1 mol % reactive groups in sericin and 21.3 mol % reactive groups in fibroin are available for reaction. In the absence of protecting groups, the isocyanate reaction modifies any hydroxyl, amine, or carboxylic acid-terminated amino acids. By incorporating a reagent (e.g. 2-ICEMA) in stoichiometric amounts, partial conversions of reactive groups can be conducted to allow versatile processing.

With the introduction of certain moieties, the solubility characteristics of fibroin change significantly. Methacrylate, for example, presents highly hydrophobic alkene and carbonyl groups at modified amino acids. As a result, the fibroin conjugate is no longer soluble in water or a LiCl/DMSO solution. Among numerous tested organic solvents (e.g. ethanol, 2,2,2-trifluoroethanol, chloroform, and dichloromethane) and salt/solvent systems (e.g. <8M LiBr/$H_2O$, <1M LiCl/DMSO), 1,1,1,3,3,3-Hexafluoro-2-propanol (HFIP) was the only solvent to provide solubility for fibroin-methacrylate conjugates. HFIP is therefore a good carrier for further characterization of fibroin conjugates, as well as for deposition of fibroin-methacrylate for further experimental steps. Other solvents which were not tested but which provide solubility for fibroin conjugates or sericin conjugates may similarly be used.

In contrast to fibroin/fibroin conjugate, sericin conjugate has an advantage (in certain embodiments) of retaining a high degree of water solubility characteristic of native sericin. This may enable patterning sericin microstructures using environmentally friendly aqueous solvents (including water alone), It is important to note, however, that this advantage pertains to individual sericin conjugate molecules (i.e. monomers) and not photopolymerized structures comprising crosslinked sericin conjugate. Thus, the sericin conjugates may be handled with environmentally friendly aqueous solvents, and then patterned using the photoactive moiety and one or more photoinitiators to produce a densely crosslinked micropattern structure.

Photopolymerization, and in particular photolithography, is established as a versatile tool for producing controlled architectures in fields such as the manufacture of transistors. According to the present invention, photolithography provides for direct patterning of silk with as few as a single masking step and a single radiant energy exposure step (e.g., UV, Vis, IR, etc.). Similar to a photoresist, the silk conjugate can be transformed physically from polymer fibers that are less rigid to a more rigid, patterned, crosslinked structure via crosslinking through the photoactive moieties on adjacent polymer chains of silk conjugate. While the process is robust and allows for multiple masks and exposures if desired, the process can also be practiced in an efficient manner which avoids many of the subsequent steps conventionally required for producing positively and negatively-patterned architectures in the general field of lithography. The inventive patterned silk microfabrication technique is advantageous for its ability to rapidly produce directly micropatterned surfaces and structures through light exposure methods in a single step process if desired (i.e. a micropattern or micropatterned structure can be produced in a single radiation or photoexposure step). Well-established techniques and materials (e.g. masking materials) may be employed in accordance with the teachings herein for producing such microstructured features of silk protein.

Figure 3A:
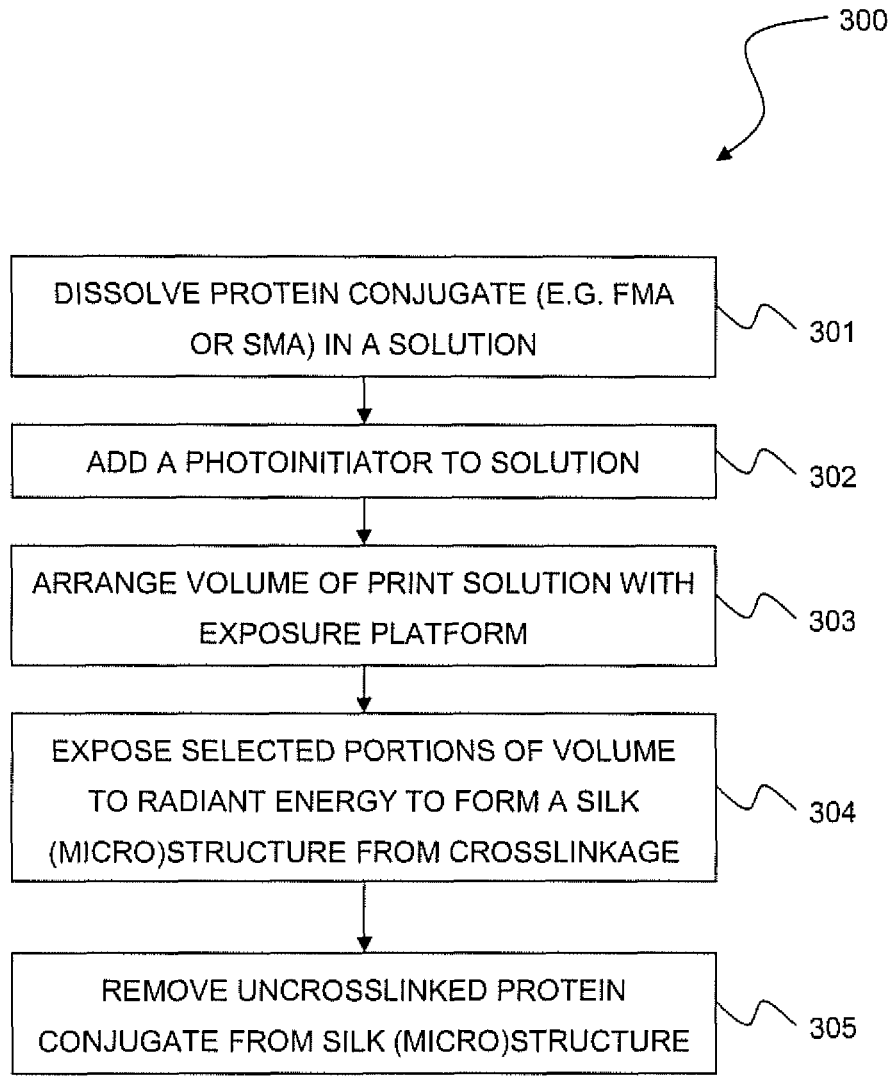
FIGS. 3A and 3B are flowcharts of methods for photopolymerization of biomaterial structures from photoactive silk proteins.

FIG. 3A is a flowchart of a method 300 for photopolymerization of biomaterial structures (e.g. microstructures) from silk proteins. Generally, photopolymerization may be accomplished through radiation-induced (e.g. UV-induced) polymerization of any silk based photopolymer-containing chemical moieties (i.e., chemical groups that crosslink on exposure to light). At step 301, a solid (e.g. powdered) photoreactive silk protein conjugate (e.g. a fibroin conjugate such as FMA or a sericin conjugate such as SMA) is generally first dissolved in a solution. The silk conjugate necessarily includes one or more photoreactive moieties together with the core sequence of natural fibroin protein or natural sericin protein. Generally, a photoinitiator would be added at step 302; however in some embodiments it may be possible to initiate crosslinking of the photoactive moiety in neighboring silk conjugates without a separate photoinitiator. A variety of known photoinitiators may be used in the practice of the invention. Various classes of photoinitiators for UV curing include but are not limited to—hydroxyalkylphenones, acyl phosphine oxides, benzil ketals, benzophenone derivatives, thioxanthone derivatives, benzoin derivatives, alpha hydroxyketones (e.g. Irgacure 184, Irgacure 2959 and Ciba DAROCUR 1173) and alpha amino ketones (e.g. Irgacure 907, Irgacure 1300). Similarly, Bis Acyl Phosphine Oxide (BAPO) type of photoinitiators such as Irgacure 819 are especially designed to be activated by longer wavelength UV light in the near visible region above 430 nm. Other known photoinitiators include benzoin, benzoin alkyl ethers, benzophenone, anthraquinone, benzil, Michler's ketone, and a mixture of biimidazole and Michler's ketone. Compounding systems such as biimidazole and dialkylaminostyryl derivatives, S-triazine and cyanine derivatives, and S-triazine and thiapyrylium derivatives may also be used.

After photoinitiator has been added to the silk protein conjugate, the resulting solution may be referred to as a print solution per its readiness for either two-dimensional (2D) or three-dimensional (3D) printing by photopolymerization. In some cases where the photoinitiator may not be required, the solution of silk protein conjugate would be a print solution. At step 303, a volume of the print solution is arranged for photoexposure on an exposure platform. For 2D printing, arrangement at step 303 generally comprises casting of the solution on a substrate (i.e. the exposure platform). Casting can be achieved by any of a variety of techniques including spin coating, spray coating, dip coating, etc. For 3D printing, arrangement at step 303 may comprise arranging the print solution in a container having length, width, and height dimensions at least as large as the respective length, width, and height dimensions of the silk structure to be produced. Multiple techniques for 3D printing are known, the applications of which at step 303 will be apparent to those of skill in the art. Some examples are provided in greater detail below.

At step 304, selected portions of the volume of print solution are exposed to radiant energy. The radiant energy wavelength(s) may vary between alternative embodiments, including but not limited to the ultraviolet (UV) spectrum, near-UV spectrum, visible light, infrared (IR), and others wavelength ranges within the electromagnetic spectrum. Appropriate wavelength ranges may be selected according to the wavelengths with which the photoinitiator and photoreactive moieties react. Selective photoexposure at step 303 may take a variety of forms, including selectively blocking exposure with a photomask. Alternatively, some 3D printing methods simply use devices which deliver radiant energy to highly specific and controlled locales.

Silk protein conjugate in the selected portions of the volume of print solution which are exposed to radiant energy at step 304 form a crosslinked structure. Those portions of the volume of print solution which are not exposed to radiant energy retain unaltered uncrosslinked protein conjugate. At step 305, such uncrosslinked protein conjugate is removed.

Figure 3B:
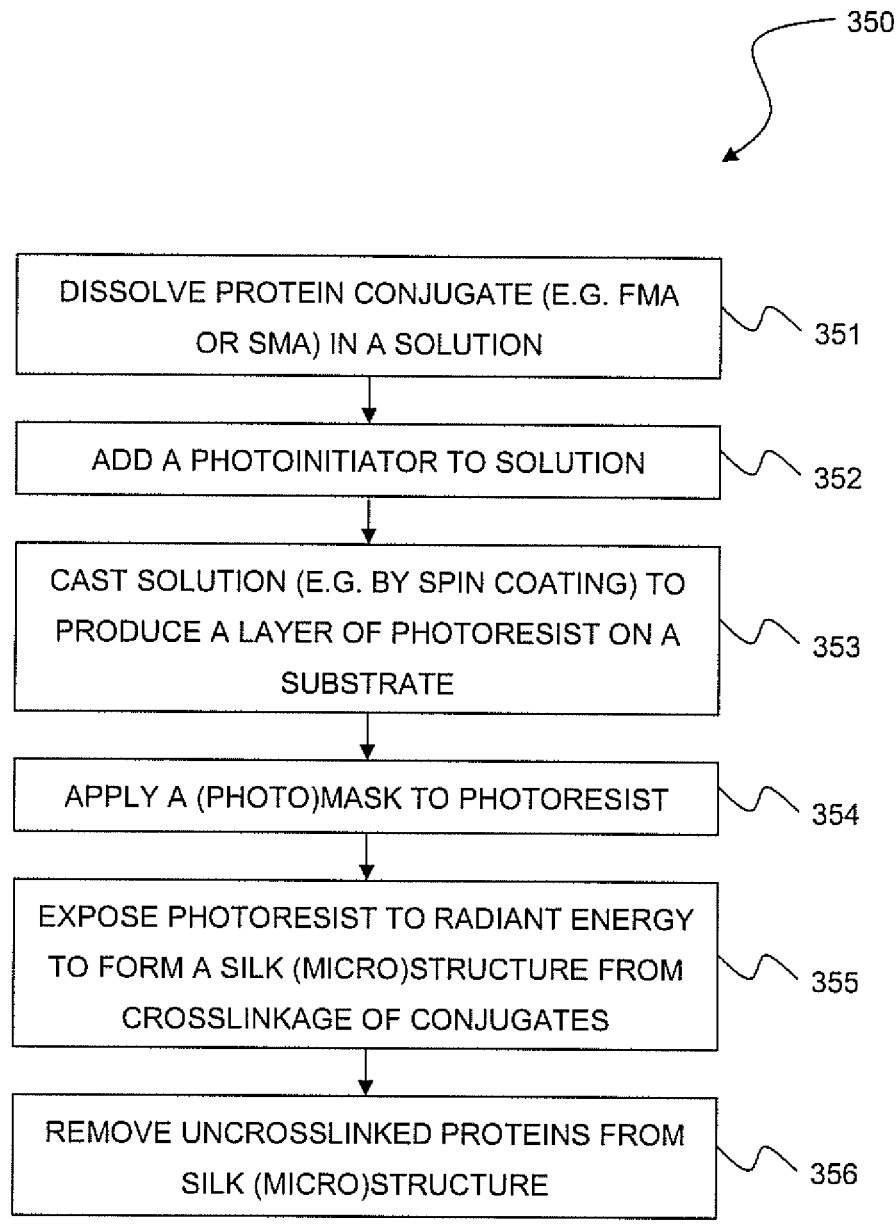

FIG. 3B shows a photolithography method 350 consistent with method 300 of FIG. 3A, except here details are provided which are pertinent to 2D printing as particular example. In the case of 2D printing, the print solution may be called a casting solution. Photoreactive protein conjugate is dissolved and combined with photoinitiator at steps 351 and 352, respectively. The casting solution is cast at step 353 onto a substrate (the exposure platform) to produce a layer or film of casting solution. The substrate may include a release layer for eventual separation of the crosslinked protein from the substrate. One exemplary casting method is by spin coating to produce a thin uniform layer. Other methods of casting at step 353 include but are not limited to pouring, dip coating, and spraying. If needed or desired, excess solvent or solution may be removed from the substrate such as by evaporation. A (photo)mask is applied to the cast layer of solution, which may be referred to as a photoresist, at step 354. The mask is configured to block some portions of the photoresist from radiation exposure while leaving other portions of the photoresist exposed to radiant energy. This allows for imparting of a particular intended structure to the final crosslinked protein structure. Once the mask is applied, the layer/photoresist is exposed to radiant energy at step 355. The exposure duration and wavelength at step 355 may vary, but examples include 1.0-3.0 second exposure times and a wavelength range of 320-500 nm. This forms a silk structure (e.g. microstructure) from crosslinkage of fibroin or sericin conjugate molecules exposed to the radiant energy. Those conjugate molecules which are not exposed to the radiant energy (e.g. due to the mask) do not undergo crosslinkage. Such uncrosslinked protein conjugates are removed from the crosslinked protein structure at step 356. This is akin to and may be referred to as developing or development of the photoresist (i.e., separation of the crosslinked silk and the uncrosslinked silk conjugate).

As a particular example, fibroin-methacrylate (FMA) was dissolved at 4% (w/v) in HFIP, and 0.5% (w/v) of the photoinitiator Irgacure 2959 was added. This solution was cast onto Si/glass substrates and the HFIP allowed to dry for 5 minutes prior to UV exposure (Lumen Dynamics OmniCure 1000 system, 1.0 sec exposure using a 320-500 nm filter). Following this, the residual HFIP was allowed to fully evaporate over a period of 12 hours. Uncrosslinked protein was removed by a developing step. This consisted of immersion of the substrate in a 1M LiCl/DMSO solution for 2 hours followed by copious rinsing with deionized water to reveal protein patterns. Substrates were then dried in a gentle stream of $N_2$.

In the case of sericin protein conjugate, dissolution of protein conjugate at step 301 and removal of uncrosslinked protein conjugate at step 305 in FIG. 3A may be accomplished with water as the primary or only solvent. This has meaningful environmental advantages. As indicated above, sericin conjugate monomer retains a high degree of water solubility characteristic of native sericin. When sericin conjugate monomers are exposed to light (e.g. UV light) in the presence of a photoinitiator (e.g. Irgacure 2959), the conjugate becomes insoluble in water—a transition which is attributed to chemical crosslinking between large constituent polypeptide chains of the sericin protein. Thus, development at step 305 would remove the cast yet still water soluble conjugate which is not crosslinked, but would not immediately remove the molecules of the crosslinked sericin conjugate structure cured by exposure to the radiant energy.

Figure 4:
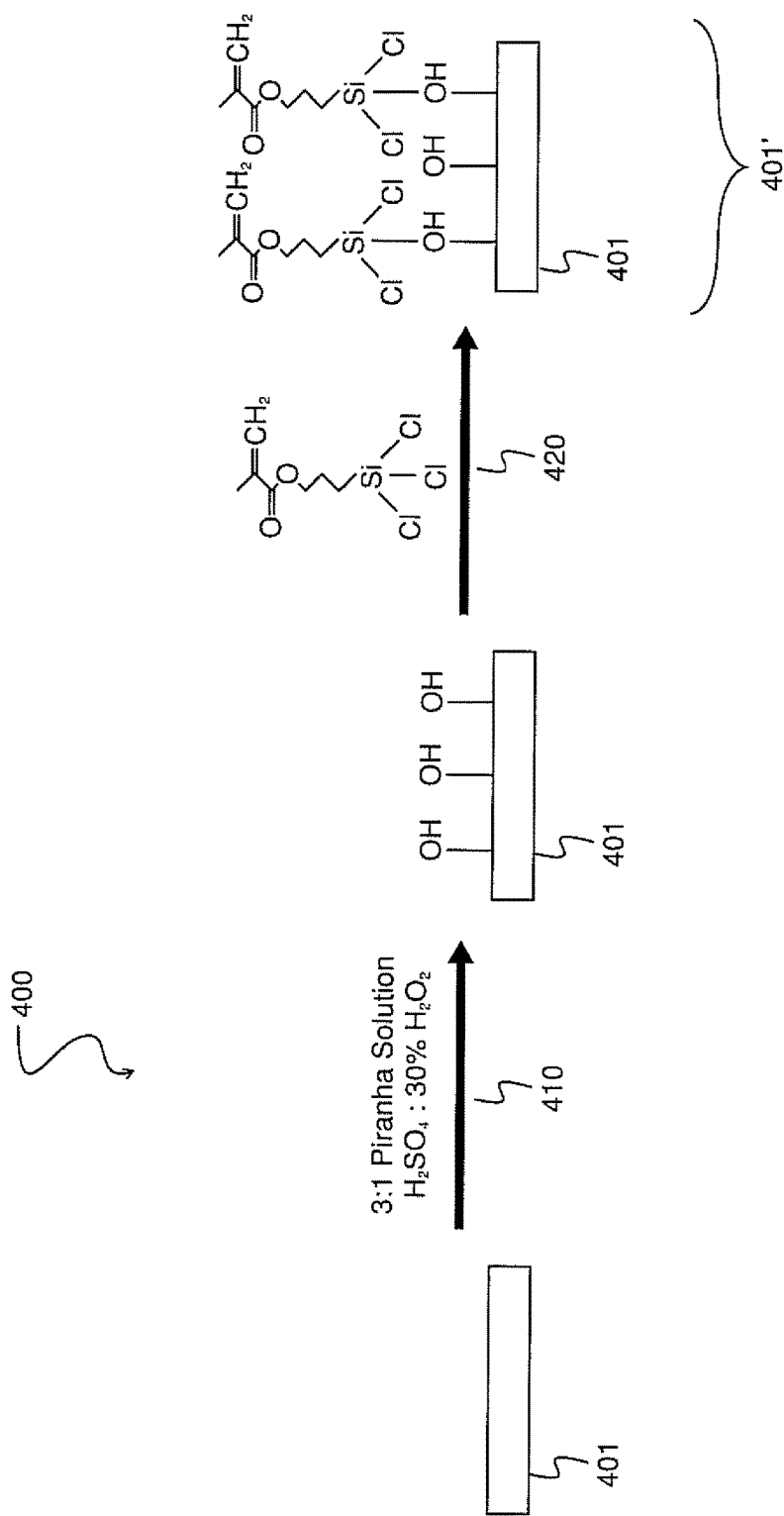
FIG. 4 shows surface functionalization for a substrate which may be used for methods of photopolymerization.

A substrate may be prepared according to the process 400 shown in FIG. 4. A substrate 401 (e.g. silicon wafers or glass surfaces or biocompatible material surfaces (e.g., biocompatible metals or metal alloys, biocompatible plastics or ceramics, etc.) any other surface of interest) can be, if necessary, modified to present reactive functionalities/groups for (covalent) protein bonding to the surface, a process generally referred to as surface functionalization. The substrate 401 is first treated to remove organic contaminants and hydroxylate the surface as shown at step 410. This may be accomplished with, for example, a Piranha solution of 3:1 98% $H_2SO_4$:30% $H_2O_2$. This may be followed by repeated washing (e.g. with deionized water and ethanol) and then drying (e.g. at 150° C.). Functionalization is then accomplished at step 420 with an appropriate functionalizing solution. As an example, the surfaces of substrate 401 can be functionalized with 3-(trichlorosilyl)propyl methacrylate (TPM) if the protein conjugate is fibroin-methacrylate (FMA) or sericin methacrylate (SMA). The final output of process 400 is functionalized substrate 401'. The following are exemplary step-by-step processes:

One or more surfaces of substrate 401 are treated with 1 mM TPM in a 4:1 solution of heptane:carbon tetrachloride, and allowed to react for 5 minutes at room temperature.

Alternatively, squares of silicon or glass substrate 401 may be functionalized with TPM by means of a vapor deposition technique. 0.5 mL TPM is added to a desiccator maintained at 0.1 bar for 16 hours. This allows the TPM to react and present covalently bound functional groups. Modified substrates (presenting Si-methacrylate groups) are then washed with hexane and water and dried before further use.

Figure 5:
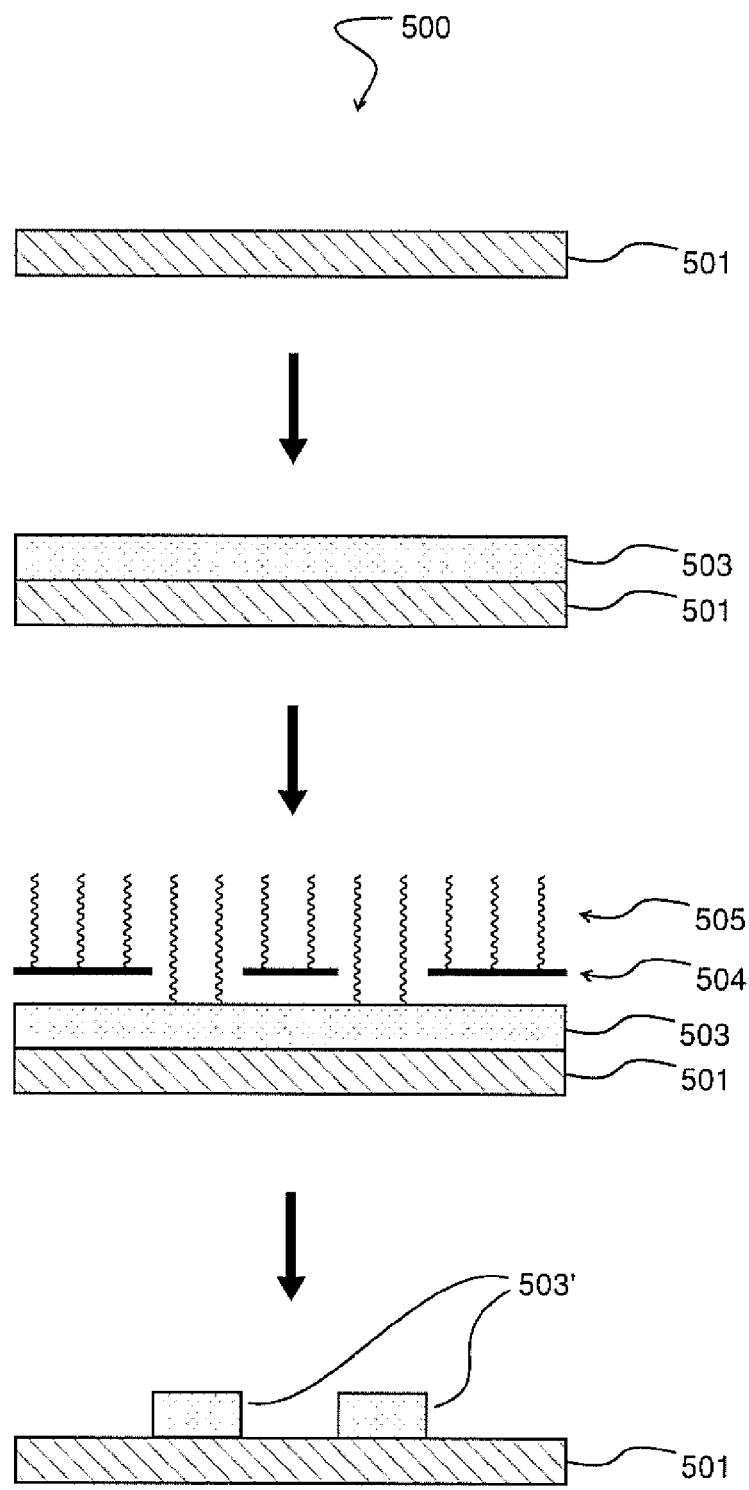
FIG. 5 is a diagram showing photolithography of photoactive protein.

FIG. 5 provides a diagram consistent with method 300 of FIG. 3A and, more particularly, method 350 of FIG. 3B. A substrate 501 may first be modified as necessary or desired to present functional groups for protein bonding to the surface (e.g. see FIG. 4). In the photolithography process 500, a solution of photoactive silk protein is cast onto a substrate 501 so as to create a film/layer 503. This may be accomplished by various known casting techniques. As one example, spin-coating produces a thin, uniform layer 503 of protein solution. Next, a (photo)mask 504 is applied. Mask 504 is a patterned mask selected according to the pattern which is to be imparted to the final silk protein structure. The mask could be a preformed metal, opaque plastic or ceramic material, or alternatively, the mask could be created on top of the layer 530 (e.g. it could be a photoresist material which is patterned and then used as a mask). The spacing between a mask 504 and layer 503 may vary according to different embodiments. However, experimental evidence shows improved resolution of the resulting crosslinked structure with smaller gaps. Preferably, mask 504 is in contact with layer 503 (i.e. there is no gap). (Note that mask 504 and layer 503 are not shown in contact in FIG. 5, serving the practical purpose of clearly illustrating the two distinct elements). The layer 503 is selectively exposed to radiant energy 505 to crosslink proteins in the photoresist/layer 503. The radiant energy 505 may vary in wavelength, intensity, and exposure time according to the photoreactive moiety of the fibroin or sericin conjugate or the photoinitiator chosen. In a particular example case, high-intensity UV light in the wavelength range of 320 to 500 nm was employed with an exposure time of 1 second. Light sources for exposure suitably applicable to the composition of the present invention include general purpose light source capable of emitting ultraviolet and visible light rays having wavelengths over 180 nm such as, for example, high pressure mercury lamps, xenon lamps, metal halide lamps, fluorescent lamps, tungsten lamps, argon ion laser, helium cadmium laser, krypton laser and the like.

Finally, the photoresist/layer 503 is subjected to a development step, in which a solvent dissolves uncrosslinked protein conjugate molecules leaving crosslinked patterns 503' on the substrate 501. In these experiments, the protein is treated as a negative photoresist that crosslinks in the presence of UV light and a photoinitiator.

In a particular example, initial casting of the protein layer/film for photolithography was achieved through dissolution of fibroin-methacrylate (FMA) along with the photoinitiator in HFIP. This solvent provides stabilization of α-helical conformations when the protein is unfolded. Constituent alkyl halide groups ($CF_3$) have a high electronegativity and can substitute for hydrogen bond donors to effectively solvate proteins. In addition, HFIP might induce a conformational change in fibroin from native, β-sheet-rich structure to α-helical conformation, enabling facile dissolution. Two photoinitiators, Darocur 1173 and Irgacure 2959, were assessed for solubility and functionality in the protein solution. Solutions were cast onto methacrylate-conjugated silicon substrates, and the solvent was allowed to evaporate briefly to immobilize the protein during UV exposure. The liquid photoinitiator Darocur 1173 was observed to produce phase separated droplets during the process of film casting. Therefore, Irgacure 2959 was selected as a preferred photoinitiator. Other photoinitiators may also be used as discussed above with FIG. 3A.

For possible use with at least those embodiments involving fibroin-methacrylate (FMA), a number of solvent systems were evaluated to determine how to best remove uncrosslinked FMA. HFIP is observed to readily remove protein, exposing bare silicone, yet it can result in considerable swelling and deformation of crosslinked features. This is likely due to the high degree of permeability of the crosslinked network to HFIP, which is still able to disrupt hydrogen bonding. Trifluoroethanol (TFE) is one degree below HFIP in terms of solvation potential, possessing one less $CF_3$ moiety. FMA is observed to be insoluble in TFE, yet blends of HFIP/TFE as low as 75% HFIP are able to develop uncrosslinked protein over a period of 24 hours. This produces notable development. Alternatively, a system of LiCl in DMSO was found to be an ideal solvent for the development of unexposed regions of protein photoresist, at least in the case of fibroin-methacrylate (FMA). In comparison to solutions of LiBr in DMSO, LiCl is likely more efficient in dissolving the FMA conjugate.

For some embodiments, contact photolithography (with contact being made between layer 503 and mask 504) is conducted in an inverted orientation from that which is shown in FIG. 5. Specifically, layer 503 is dried and substrate 501 together with layer 503 is inverted and placed atop mask 504 with a lamp situated below, projecting radiant energy 505 upward. This technique minimizes deformation of layer 503 when in contact with the mask 504 in addition to facilitating removal of the substrate 501. As a result, the theoretical minimum resolution of contact exposure is <1 μm.

Figure 6:
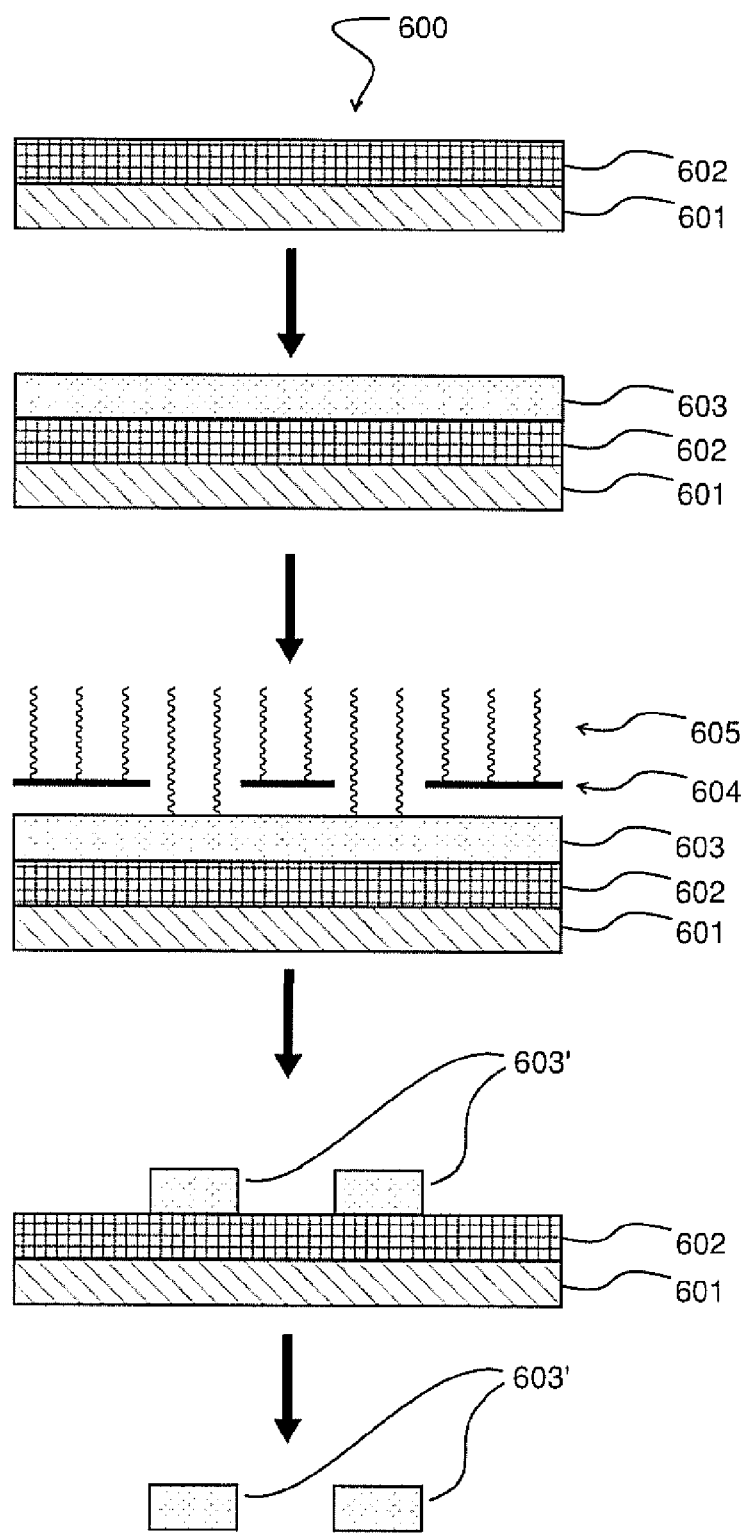
FIG. 6 is a diagram showing photolithography of photoactive protein where a release layer is used.

FIG. 6 is a diagram showing a photolithography process 600 with silk protein conjugate in which it is possible to separate the patterned silk structure 603' from the substrate 601. Process 600 bears substantial similarity to process 500 of FIG. 5, although a major difference is use of a release layer 602. Casting solution containing a fibroin or sericin conjugate is cast into a film/layer 603 atop release layer 602 which is supported by substrate 601. The use of release layers is well known in the general art of lithography. Suitable release layer material selection will occur to those of skill in the art. Exposure of the layer 603 to radiant energy 605 in conjunction with an applied mask 604 is conducted substantially the same as described above in relation to the exposure step shown in FIG. 5. Cross-linkage of protein conjugates occurs only where the protein is exposed to the radiant energy 605. Subsequently, uncrosslinked protein conjugate is removed, leaving the developed, patterned silk structure 603'. By way of release layer 602, both release layer 602 and substrate 601 can be removed so as to obtain just the patterned silk structure 603'. It is noted that FIG. 6, like FIG. 5, is a cross-sectional diagram and as such the two parts of silk structure 603' may be connected albeit in a plane different from the cross-sectional plane shown in FIG. 6.

Figure 7:
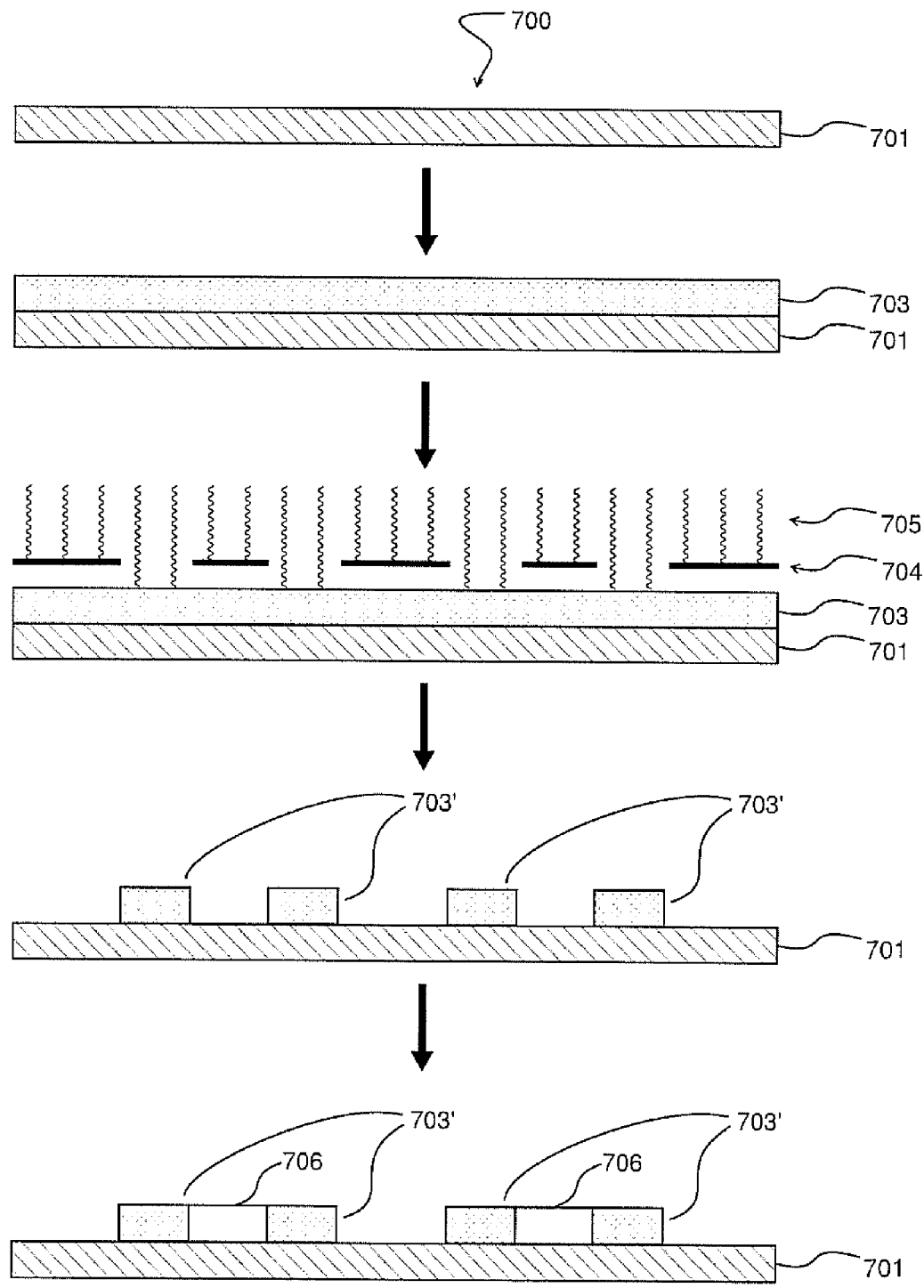
FIG. 7 is a diagram showing photolithography used in the production of biocircuits.
Figure 8A:
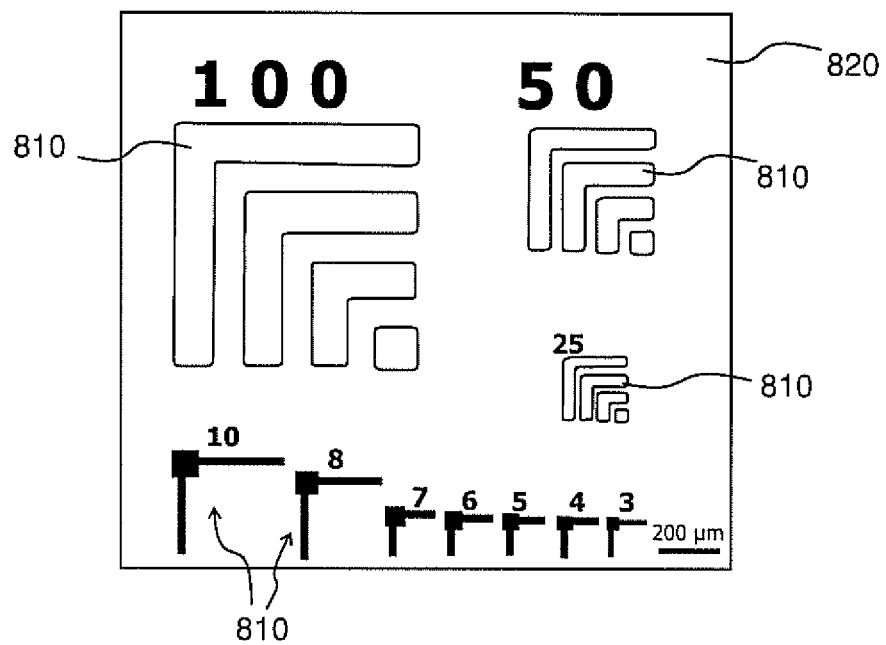
FIGS. 8A and 8B shows silk protein microstructures produced with photolithography.
Figure 8B:
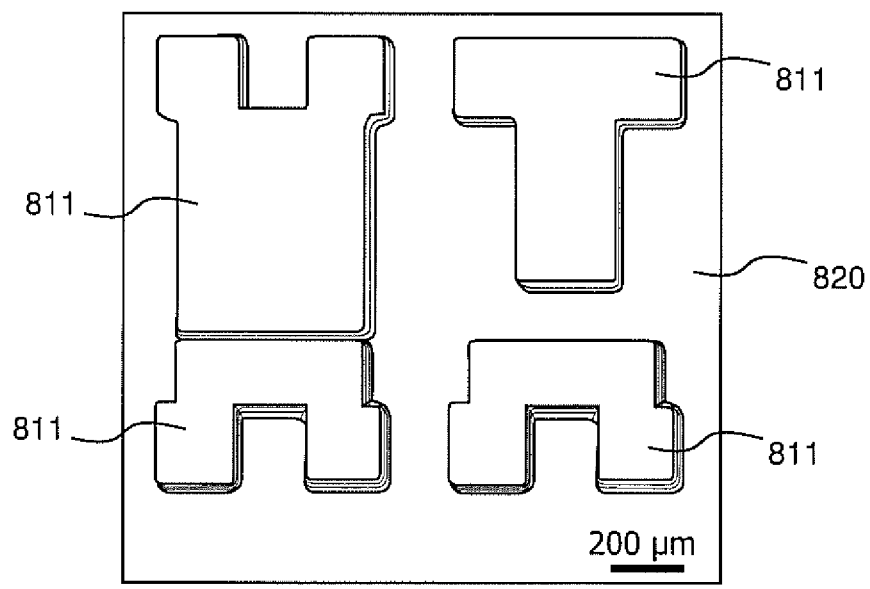

FIG. 7 is a diagram showing photolithography used in the production of microelectronics. The photolithographic process 700 is conducted in substantially the same manner as process 500 of FIG. 5. In brief summary, a silk protein conjugate casting solution is cast to form a photoresist layer 703. The layer 703 is combined with a mask 704 and exposed to radiant energy 705. Mask 704 is then removed and the layer 703 developed to remove uncrosslinked protein conjugate and yield the final silk protein microstructure 703'. At this point, in the final stage shown in FIG. 7, a conductive or semiconductive material 706 may be added within the silk microstructure (e.g. in grooves, channels, paths, etc. created by the removal of uncrosslinked protein). Material 706 may be a metal or some other conductive or semiconductive material. Conductive or, alternatively, semiconductive pathways and internal structures may thus be formed within the silk microstructure 703'. This process and variations thereon allow for creation of silk-based electronic circuits such as interdigitated electrodes. Such so called "bioelectronics" made of silk protein are generally flexible, a desirable quality in number of applications such as biomedical implants. In a similar fashion, cells, bioactive compounds of interest or other materials may be added in a manner similar to the conductive or semiconductive material 706 to yield patterned silk structures which are associated with cells, bioactive compounds of interest or other materials. In this way, implantable devices or skin contacting device can be made from patterned silk, and the devices could include cells, bioactive compounds or other materials of interest FIGS. 8A and 8B show two drawings representative of SEM images of patterned silk structures made from silk protein conjugate according to the invention. More particularly, in FIG. 8A each of the four right angle structures under each of the "100", "50", and "25", respectively, as well as the seven right angle structures across the bottom are microstructures 810 of fibroin conjugate having methacrylate as a photoreactive moiety. The same is true of the four microstructures 811 in FIG. 8B. Similar structures and patterns can be produced from sericin photoactive conjugate, although the material properties (in particular the strength/modulus) will vary. Silk microstructures 810 and 811 were produced with contact photolithography in accordance with method 350 of FIG. 3B. The angle of the SEM image in FIG. 8B shows the third dimension of the microstructures 811, namely height in a direction perpendicular to the surfaces of substrates 820. Microstructures 811 are patterned/configured as biomaterial films of predetermined size (that is, all width, length, and height dimensions and the final shape were pre-selected). These films are generally flexible, free-standing optically transparent films. Uncrosslinked protein conjugate has been removed such that the surface surrounding microstructures 810 and 811 are the surfaces of substrates 820 onto which the casting solution of protein conjugate was initially cast prior to irradiation with UV light and resultant cross linkage of fibroin conjugate molecules. By controlling the thickness of the protein layer (from the casting solution) deposited on the substrate 820, structures of varying height in three dimensions can be created. Patterns ranging from ~250 nm to several microns in height are easily fabricated in this manner. The scalability of photolithography provides that large areas (several cm) with microstructural topology can be fabricated. This enables translation to large scale production of micropatterned silk substrates or macroscale objects with micro and nanoscale control. Using attachment groups that can be subsequently cleaved, independent and unattached shapes of fibroin or sericin can also be formed.

After fibroin-methacrylate (FMA) was patterned, the resulting micro and nanostructures of silk were imaged using AFM in addition to SEM to characterize surface morphology and fidelity of architectures formed. AFM analysis provided evidence of the ability to form features of controlled height by varying the thickness of the deposited protein conjugate.

Using photolithography, silk protein features can be patterned at sub-microscale resolution (≤μm) over macroscale areas (e.g. several cm). AFM and SEM imaging show microscale patterns in three dimensions (3D) can be formed at least in the size range of 1-100 μm in a height dimension (i.e. perpendicular to a substrate surface). Films and other structures of thicknesses greater than 100 μm are also possible. Resolution in a dimension parallel with the substrate (e.g. a line width) may be at least as small as 3 μm.

Periodic and biodegradable silk protein structures of microscale features can be formed over macro-scale areas (up to a centimeter or more) to form structurally-induced iridescent protein holograms in complex patterns. Sericin conjugate is particularly well suited to this application, although fibroin conjugate may likewise be used. Lines, curves or interconnected shapes can be used to produce large, macro-scale arrays having thousands of similar or identical structures which may produce interesting interplay with light and optical properties. In sample designs, sericin squares of 10-50 μm were produced that create structure-induced iridescence in their respective patterns. Varying the protein loading per substrate provides the ability to create features of well-defined height profiles, producing features ranging from sub-micrometer height upwards to tens of micrometers.

Embodiments of the invention can be employed as novel sensor labels and optical materials. As the patterned crosslinked silk is biodegradable, the invention allows for a number of products previously unattainable. Silk microstructures can function as bio-friendly cellular substrates for the spatial guidance of cells without mandatory use of cell-adhesive ligands. The scalability in height and feature aspects allows the fabrication of thin microstructures, appropriate for cellular adhesion, up to thick-walled microwells. The high mechanical strength, particularly of fibroin, and controllable degradation of silk protein conjugate (from either fibroin or sericin) provides opportunities in fabricating sustainable, nanostructured scaffolds and flexible microdevices. One microstructure which may be patterned is a grid. As just one example case, fibroin was patterned in the form of a grid with 20 μm lines that form 200 μm squares. Many possible patterns may be used with biological tissues. Grids of a wide range of sizes and configuration could be made for spatial patterning of cells according to the protein conjugate manufacture and silk protein structure photopolymerization discussed above.

Samples of fibroin conjugate microstructures were tested for such a cellular adhesion application. Murine fibroblasts (L-929) cells were seeded on micropatterned silk protein structure surfaces (1500 cells/cm$^2$) and incubated at 37° C. for 3 days. (Such specifics for seeding of cells may be varied, as will be apparent to those in the art.) Cells tended to preferentially attach to the fibroin protein patterns in comparison to the surrounding surfaces (e.g. glass and silicon). Further, focal adhesion (FA) of the fibroblasts to the underlying fibroin micropatterns was observed by staining protein complexes containing vinculin. (Such chemical reactants are available from, for example, Sigma-Aldrich in St. Louis, Mo.) These structural membrane-associated FA complexes function as nucleation sites for actin filaments connecting the extracellular matrix (ECM) on the outside to the intracellular actin cytoskeleton. Cells were observed to be well anchored to the patterned fibroin showing that fibroin conjugate patterns can be used to spatially micropattern and direct cells. Generally, organic and inorganic molecules can be coupled to enhance fibroin and sericin applications for cell guidance on micro and nanostructured wires and scaffolds.

Cellular adhesion applications are possible with sericin protein conjugate structures as well. In a particular example, osteoblast cells displayed preferential migration and adhesion to micropatterned sericin (conjugate) architectures, effectively demonstrating the ability of sericin to selectively promote adhesion in a desired pattern. Via fluorescence microscopy, osteoblasts tended to specifically follow the 'protein grid', eventually producing a repeating architecture on top of the sericin conjugate scaffold. Here, the preservation of serine-rich repeats, implicated as regions for cellular interactions, enabled the sericin patterns to actively promote adhesion and proliferation. Specific adhesion to the scaffold could be directly attributed to bioactive properties of sericin. A low surface roughness (~3 nm) of the sericin features is further implicated in this preferential adhesion of osteoblasts, which are known to display a marked improvement in integrin adhesion on low-roughness surfaces.

Fibroin extracted from different cocoon harvests were tried over several months with identical results, showing that potential variability across different batches of naturally sourced materials should not have an affect on the silk protein conjugate and silk protein structures formed from patterning of silk protein conjugate.

Production of crosslinked structures such as by photolithographic processes 300 and 350 of FIGS. 3A and 3B includes multiple approaches by which the amount of crosslinking and the density of a resulting crosslinked structure may be selectively controlled. By controlling the precursors and the photo crosslinking steps, it is possible to tune the mechanical properties of a silk protein photoresist a final crosslinked structure. Two primary methods of varying the extent or degree of crosslinking are by regulating the degree of reaction/substitution of variable R groups of the silk protein with a photoreactive moiety and regulating the amount or concentration of photoinitiator added to the protein conjugate solution to form the casting solution.

Controlling the degree of photoactive moiety substitution is one mode of selecting or "tuning" crosslinking density of architectures. At the step of reacting dissolved protein with a photoreactive moiety, a higher stoichiometric ratio of photoactive moiety to variable R groups will increase the amount of substitution. Greater substitution provides a higher concentration of photoreactive moieties in the casting solution and thus results in greater crosslinkage and density of the final crosslinked protein architecture.

For both fibroin and sericin in general, it is desirable in many embodiments that at least 20% of variable R groups are reacted and substituted with photoreactive groups. In some embodiments, substitution of at least 50% or at least 80% of variable R groups may be substituted. Indeed, the maximum substitution which may be employed is theoretically 100% substitution, although such complete reaction is generally not practical nor is it necessary. Generally, a stoichiometry of 2.3 moles of 2-ICEMA to moles of primary hydroxyl-containing amino acids is desired in order to achieve a desired minimum degree of substitution for sericin. This preserves the fundamental bioactive properties of sericin, leaving the bulk of serine groups untouched to preserve regions associated with favorable cellular interactions. The presence of unmodified amino acids also enables the production of multifunctional biomaterial architectures via concurrent or subsequent modification strategies. In some embodiments, different photoactive moieties (including two or more moieties reactive to different wavelength bands of the electromagnetic spectrum) may likewise be conjugated with the same silk protein, be it fibroin or sericin.

An increase in photoinitiator concentration in the casting solution also results in an increase in crosslinking density. In a particular example using FMA, a low photoinitiator concentration (0.03% w/v) was found to impart a modulus to the FMA film similar to that of native fibroin. The modulus increases approximately linearly at 0.1% and 0.2% initiator up to ~16 GPa at 0.6%. In experiments, 0.6% initiator (w/v) was found to be an exemplary photoinitiator concentration to obtain well-developed microstructures via photolithography. Nanoindentation studies were conducted on films cast from fibroin, fibroin-methacrylate, sericin, and sericin-methacrylate. Indentation experiments were conducted in two modes—constant force and constant indent (indenting the samples to a depth of 10 nm). The mechanical testing of these materials indicates a significant increase in elastic modulus. The elastic modulus for fibroin was measured to be 11.0±0.9 GPa, a value that is close to its reported values as one of the strongest and toughest natural fibers. Photocrosslinked fibroin conjugate (0.6% w/v crosslinker) was measured to have an elastic modulus of 15.6±1.1 GPa. For sericin, which is not a very mechanically strong protein, crosslinked sericin conjugate showed an elastic modulus of 0.67±0.11 GPa, which was slightly (~7%) higher than that of native sericin (0.63±0.07 GPa). Overall, the values show that the mechanical strength of photopolymerizable fibroin is comparable to and possibly greater than native fibroin alone. This offers possibilities in using fibroin conjugate such as FMA for load bearing applications such as bone tissue engineering.

An advantage of manufacturing crosslinked structures of fibroin conjugate (e.g. FMA) or sericin conjugate (e.g. SMA) according to a selected degree of crosslinkage is selectable ("tunable") degradation behavior. Controlled variation of the mechanical properties of silk protein conjugate structures coupled with direct cellular attachment on a degradable, yet mechanically strong matrix without the use of cell adhesion peptides (e.g. RGD) offers new possibilities in using such crosslinked material of silk protein for load bearing applications such as bone tissue engineering.

Fibroin conjugate shows improved resistance to degradation in the presence of water as compared to regular unconjugated fibroin. In a particular test case, fibroin was found to be highly water-soluble once cast from HFIP. When fibroin films are exposed to water, fibroin readily dissolves. In contrast, crosslinked FMA films are intact and relatively unchanged even after a 7 day period. Fibroin or sericin conjugate structures according to the invention can provide controlled degradation in vitro, with applications included tissue engineering scaffolds, bone replacements, drug delivery vehicles, and photonic crystals.

As previously identified, photopolymerizable groups can include acrylates, methacrylates, and vinyl ethers. Photodimerizable groups which may also be used include cinnamates, diazirines and aryl azides. These groups can be added by taking advantage of the following chemical conjugation techniques specific to proteins:

Isocyanate Addition: Isocyanate (—N=C=O) is reacted primarily with hydroxyl-containing residues serine, threonine, and tyrosine, to form urethane linkages, in addition to reacting with primary amines such as lysine, to form urea linkages, and carboxylic acid groups aspartic and glutamic acid, to yield amide linkages.

NHS Crosslinking: Primary amine-containing amino acid lysine may be directly reacted with NHS-containing monomers to yield a chemical linkage.

Primary Amine Crosslinking: Imidoester crosslinking of an imidoester with primary amines in the protein under alkaline conditions, to yield a covalent linkage. Alternatively, reaction of pentafluorophenyl ester or hydroxymethyl phosphine with amine-containing residue lysine.

Crosslinking of Sulfhydryls: Reaction with haloacetyls, maleimides, or pyridyl disulfides to form linkages to cysteine —SH moieties.

Glycoprotein Crosslinking: The presence of aldehyde and ketone-containing sugars in the glycoprotein structure presents reactive carbonyl groups (C=O). Hydrazines and alkoxyamines may achieve such reactions.

The formation of a photopolymerizable silk biomaterial (e.g. FMA) opens up new avenues in the fabrication of diverse architectures including nano and micro particles and complex 3D architectures that are not attached to a substrate. An example is the Particle Replication in Non-wetting Templates (PRINT®) process that enables the fabrication of particles with precise control over the shape, size, composition, and surface functionality. Photopolymerizable silk protein conjugate as taught herein may be used to form engineered micro- and nano-architectures particularly in conjunction with manufacturing techniques such as stererolithography.

Modern rapid prototyping combines tools for forming objects with computer-aided design to fabricate complex architectures. The next generation of manufacturing techniques in the form of rapid prototyping (RP) and solid free-form fabrication (SFF) involve automated and computer-controlled generation of 3D shapes. This has opened up an exciting revolution in the personalized printing of physical objects. The low cost of printing devices and predicted wider accessibility make this an exciting technology in the area of medicine with the ability to develop additive manufacturing of tissues and organs. The use of light to form precise structures confers the ability to form patterns in 2 and 3 dimensions with high-throughput and spatial and temporal accuracy. 3D architectures using photoreactive silk protein conjugate as the base material for fabrication can therefore combine manufacturing and computer aided design with protein engineering and materials science.

For example, 3D silk structures may be produced using stereolithography such as via two-photon polymerization (2PP). Generally, stereolithography uses 3D microfabrication where computer aided designs are transformed into solid prototypes. A liquid photopolymer is exposed to a highly focused laser light, where the polymer only cures at the focal point and non-irradiated areas remain liquid. This process is sequentially repeated in a layer-by-layer method until the final 3D object is formed. Once the layers of polymer harden, the platform is raised out of the remaining liquid to reveal the completed structure. Since each layer is formed individually, it is possible to conceive complex internal patterns and features as well as incorporate growth factors and ECM proteins inside the photopolymerized matrix. This approach can use a novel silk fibroin conjugate as taught herein (e.g. as produced by methods 100 and 150 of FIGS. 1A and 1B) with a light-activated "direct-write" process based on 3D printing stereolithography for fabricating material of precise shape and topology. Silk-based natural proteins will be polymerized in place using light and form microstructured architectures at high throughput. Thus new precisely engineered biocompatible structures are made possible. Shapes including particles, membranes, scaffolds, wires, rods, and complex 3D structures can be formed in this manner. Nano and microparticles can be engineered in different shapes as delivery agents for therapeutics. Nano and microstructured biodegradable scaffolds can be used for tissue and bone replacement.

While the invention has been described herein with respect to various exemplary embodiments, those of the skill in the art will recognize that the invention can be practiced with modification within the spirit and scope of the appended claims.

What is claimed is:

1. A method of making photoactive silk protein, comprising the steps of:
   dissolving a silk protein selected from the group consisting of fibroin and sericin in a solvent;
   reacting in a solution said silk protein dissolved in said solvent with a reagent including at least one photoreactive moiety such that said at least one photoreactive moiety couples with said silk protein at one or more variable R groups to produce a silk protein conjugate, wherein said variable R groups are selected from the group consisting of primary amines, carboxyls, sulfhydryl groups, and hydroxyls; and
   recovering said silk protein conjugate from said solution.

2. The method of claim 1, wherein said at least one photoreactive moiety is selected from the group consisting of acrylate moieties, methacrylate moieties, and vinyl ether moieties.

3. The method of claim 1, wherein said at least one photoreactive moiety includes a methacrylate moiety.

4. The method of claim 1, wherein said reagent is 2-isocyanatoethyl methacrylate (2-ICEMA).

5. The method of claim 1, wherein said solvent of said dissolving step is a solution comprising lithium chloride (LiCl) and dimethyl sulfoxide (DMSO).

6. The method of claim 1, wherein said silk protein is from *Bombyx mori* silkworm cocoons.

7. A method of making silk structures from silk protein, comprising the steps of:
   dissolving a silk protein conjugate in a solution, wherein said silk protein conjugate is a conjugate of silk protein selected from the group consisting of fibroin and sericin having at least one photoreactive moiety;
   adding a photoinitiator to said solution to form a print solution;
   arranging a volume of said print solution on an exposure platform;
   exposing selected portions of said volume of said print solution to radiant energy to form a silk structure with crosslinkages polymerized at said at least one photoreactive moiety where said silk protein conjugate is exposed to said radiant energy; and
   removing said silk protein conjugate from said silk structure which were not exposed to said radiant energy and which are not crosslinked.

8. The method of claim 7, wherein said reaction platform is a substrate and said arranging step comprises
   casting said print solution on said substrate to provide said volume as a layer, and
   applying a mask to said layer, said mask determining which of said selected portions of said volume of said print solution are exposed to said radiant energy in said exposing step.

9. The method of claim 8, further comprising a step of evaporating residual solution from said substrate after said step of casting.

10. The method of claim 8, wherein said step of applying a mask brings said layer into contact with said mask.

11. The method of claim 8, wherein said substrate presents methacrylate groups for protein surface bonding.

12. The method of claim 7, wherein said silk protein of said silk protein conjugate is fibroin and said dissolving step uses a 1,1,1,3,3,3-Hexafluoro-2-propanol (HFIP) solution as a solvent.

13. The method of claim 7, wherein said removing step is performed by washing with a solution of lithium chloride (LiCl) and dimethyl sulfoxide (DMSO).

14. The method of claim 7, wherein said silk protein of said silk protein conjugate is sericin and one or more of said dissolving step and said removing step uses water as a solvent.

15. The method of claim 7, wherein said adding step uses an alpha hydroxyketone as said photoinitiator.

16. The method of claim 7, wherein said exposing step uses UV light in the wavelength range of 320 to 500 nm.

17. A protein conjugate of silk protein selected from the group consisting of fibroin and sericin and having at least one photoreactive moiety, said at least one photoreactive moiety being conjugated at one or more variable R groups of said silk protein,
   wherein said variable R groups are selected from the group consisting of primary amines, carboxyls, sulfhydryl groups, and hydroxyls and wherein said protein conjugate of silk protein is dissolved in a solvent comprising LiCl and DMSO.

18. The protein conjugate of claim 17, wherein said at least one photoreactive moiety is selected from the group consisting of acrylate moieties, methacrylate moieties, and vinyl ether moieties.

19. The protein conjugate of claim 17, wherein said at least one photoreactive moiety includes a methacrylate moiety.

20. A patterned structure formed from a silk protein conjugate of silk protein selected from the group consisting of fibroin and sericin and at least one photoreactive moiety, wherein said patterned structure is crosslinked at said at least one photoreactive moiety and is configured in a microscale pattern.

21. The patterned structure of claim 20, wherein said silk protein of said protein conjugate is fibroin and said patterned structure has an elastic modulus equal to or greater than the elastic modulus of natural fibroin.

22. The patterned structure of claim 20, wherein said patterned structure is a two-dimensional patterned film.

23. The patterned structure of claim 20, wherein said patterned structure is three-dimensional.

* * * * *